Jan. 9, 1973 R. G. JELLY Plant Pat. 3,287
ROSE PLANT
Filed April 9, 1971
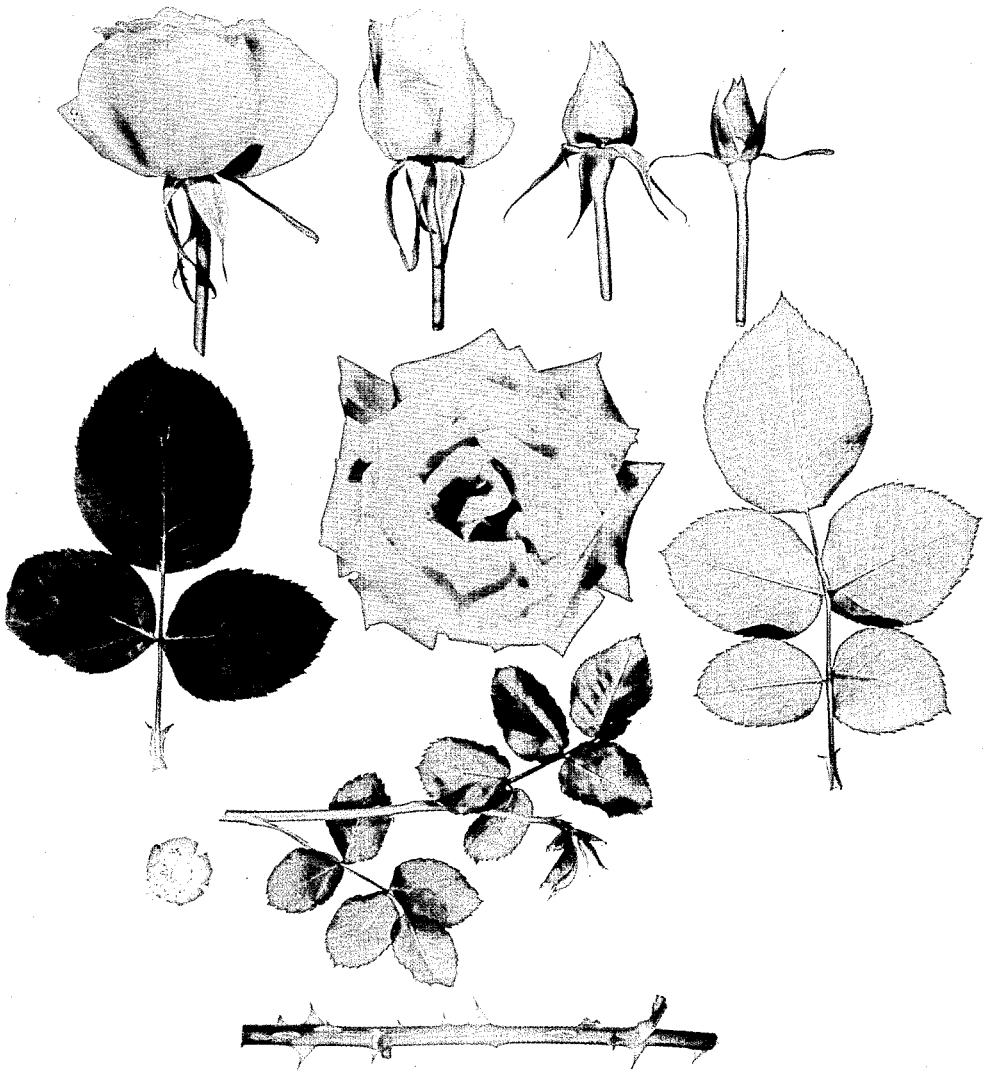
INVENTOR.
ROBERT G. JELLY
BY Rummler & Snow
Attys.

United States Patent Office

Plant Pat. 3,287

Patented Jan. 9, 1973

3,287

ROSE PLANT

Robert G. Jelly, Richmond, Ind., assignor to E. G. Hill Co., Inc., Richmond, Ind.

Filed Apr. 9, 1971, Ser. No. 132,919

Int. Cl. A01h *5/00*

U.S. Cl. Plt.—20 1 Claim

ABSTRACT OF THE DISCLOSURE

A brilliant red greenhouse rose developed for improved year-around cut flower production by crossing "Forever Yours" (P.P. #2443) with an undisseminated and unpatented red seedling, the new variety being distinguished by its improved flower color and superior flower form, its abundant and continuous production of large many petaled blooms, and its excellent winter performance with a reduced number of blind shoots.

BACKGROUND OF THE INVENTION

This new variety of rose plant was developed by me at Richmond, Indiana, through breeding efforts carried on with the object of producing a high quality red flowered greenhouse rose plant would have improved performance under the low light intensities of winters in the United States. This objective was accomplished by crossing "Forever Yours" (P.P #2,443) with an unnamed, undisseminated and unpatented red flowering seedling, identified in my breeding records as #15–61R, selected for its vigorous growth characteristics, the dark red color of its blooms, and its good winter performance under greenhouse culture. Six years of asexual propagation by grafting and under my direction at Richmond, Ind., and by budding at Livermore, California, has demonstrated that the hereinafter described distinguishing characteristics of this new variety are fixed and hold true from generation to generation.

DESCRIPTION OF THE DRAWING

My new variety of rose plant is illustrated by the accompanying photographic representation in which various stages of the bud are shown, ranging from the young bud when the sepals first divide to the half-opened flower, with a face view of the fully opened bloom, specimens of young and mature leaves at the right and left, respectively, of the full opened bloom, a portion of poung wood with leaves, a typical piece of the mature wood, and, at the left of the young wood branch, a face view of the reproductive center portion of the mature flower with the shielding petals removed. The drawing is in full color with the color rendition done as closely as is reasonably possible under conventional photographic procedures.

DESCRIPTION OF THE NEW PLANT

The following is a detailed description of my new variety of rose plant with color designations according to the R.H.S. Colour Chart, the Horticultural Color Chart by Robert F. Wilson for the Royal Horticultural Society, and Nickerson's "Color Fan," identified herein as (R), (W), and (N), respectively.

*The plant*

Origin: Seedling.

Parentage:

*Seed parent.*—Red seedling #15–61R (unpatented.

*Pollen parent.*—"Forever Yours" (P.P #2,443).

Classification: Hybrid tea.

Type: Greenhouse cultured for cut flower production (has not been tested for outside use).

Form: bush.

Growth (in greenhouse): Moderately free and vigorous.

Habit: Upright and much branched with canes of medium to large diameter.

Main stems: Color—shaded from A to B of Yellow-Green Group 146 (R).

*Thorns.*—Several to many, medium to long in length and hooked downwardly from a narrow base. Color—shaded from Greyed-Orange 165B to Greyed-Orange 164B (R).

*Prickles.*—None. *Hairs*—none.

Branches: Color—shaded from A to B of Yeldow-Green 146 (R).

*Thorns.*—Same characteristics as those on main stem. Color—from Turkey Red 721/3 (W) to brilliant Yellow-Green 2.56 Y 8/9 (N).

*Prickles.*—Very few. Color—from translucent to Chrysanthemum Crimson 824/2 (W).

*Hairs*—None.

Foliage:

*Leaves.*—Shape—odd pinnate. Size—medium to large.

*Leaflets.*—Number—3 to 5, sometimes 7. Shape—oval with cuspidate apex, obtuse base, and simply serrate margin. Texture—thick and leathery. Color—young—upper surface, shaded from B to C of Yellow-Green 146 (R). Young—under surface, suffused with venation variations from Chrysanthemum Crimson 824/1 to Chrysanthemum Crimson 824 (W). Mature—upper surface, slightly darker than Parsley Green 00962 (W). Mature—under surface, slightly greener than Lavendar Green 000761 (W).

*Rachis.*—Medium. Upper side—grooved, prickly on younger leaves. Under side—thorny.

*Stipules.*—Medium length, medium width, with points medium to long in length turning outwardly at an angle less than 90° from stem.

*The bud*

Form:

*Before calyx breaks.*—Short pointed with a conspicuous neck, foliaceous appendages on the surface of the bud and bristle-like foliaceous parts extending beyond tip of bud for a distance about equal to one-fourth the bud length.

*As first petal opens.*—Short pointed.

Size:

*Before calyx breaks.*—Medium large.

*As first petal opens.*—Medium large.

Color:

*Calyx.*—Scheeles Green 860/2 to 860 (W) at center with a suffusion of Parsley Green 00962 (W) at the tip before calyx breaks.

*Petals.*—As calyx breaks, from Oxblood Red 00823 (W) to venation much darker than Oxblood Red 00823. As first petal opens, outside, shaded from Cardinal Red 822/2 to 822/1 (W); inside, much more brilliant than Red Group 45A (R).

Sepals: Medium to long, falling soon. Color: Inside.—Shaded from Yellow Green 147C to 147D (R). Outside.—Shaded from Yellow Green 147A to 147B (R).

Opening characteristics (in greenhouse): Flower opens well. In extremely warm weather the bud size will decrease slightly; in cold weather the bloom color will have a darker red appearance.

Peduncle: Medium length and diameter. Strong and erect but with some bending on weak or small diameter canes.

*Bark.*—Almost smooth. Color—from Fern Green 0862 to 0862/1 (W).

*Thorns.*—None. *Prickles*—few. *Hairs*—None. Color of Prickles: Moderate Red 2.5 R 4/10 (N) to almost translucent.

*The flower*

Blooming habit: Continuous, free and abundant in greenhouse.

Size: When fully opened—large, 4 to 6 inches in diameter.

Form: High centered when first opened, becoming flat to slightly high centered as bloom matures. Petals are slightly rolled outward at first and become tightly rolled outward at maturity.

Borne: Usually one to a stem, occasionally 3 to 4 but disbudded to one. Flowers are borne on moderately strong stems of medium to long length.

Petalage: Very double—with 30 to 38 petals.

*Arrangement.*—Regular, with stamens sometimes showing.

*Shape.*—Outside petals—oval, apex almost always with two notches but occasionally with one notch. Intermediate petals—oval, apex almost always entire but occasionally showing one notch. Inside petals—oval to obovate, apex almost always entire, occasionally showing one notch.

*Texture.*—Moderately thick.

*Appearance.*—Inside—velvety; outside—satiny.

*Color.*—This rose is difficult to match with a flat color chart because of its velvety appearance. Thus actual colors may be modified by being generally shaded with venation variations. As for the general color effect of this rose, the newly opened flower is more brilliant than Red Group 46A (R) and the flower opened three days ranges from brighter than 46A to brighter than 46C (R). A more detailed description, from observations of greenhouse grown roses at Richmond, Indiana, on the dates indicated is as follows:

| | A newly opened flower, April 1970 | 3-day opened flower, May 1970 |
|---|---|---|
| Outside petal: | | |
| Outside surface | Much brighter than 46A (R). | Rose Red 724 (W). |
| Inside surface | Shaded from 53A to 46A (R); more brilliant than either. | Shaded from 46A to 46B (R); brighter than either. |
| Intermediate petal: | | |
| Outside surface | 52A (R) | Shaded from Rose Red 724 to 724/1 (W). |
| Inside surface | Slightly darker than 46B (R). | Shaded from Currant Red 821/1 to 821/2 (W) but brighter than either. |
| Inner petal: | | |
| Outside surface | 52A (R) | Shaded from Rose Red 724/2 to 724/1 (W). |
| Inside surface | Brighter than Currant Red 821/1 (W). | Shaded from Currant Red 821/1 to 821/2 (W) but brighter than either. |

Fragrance: Moderately strong sweetbriar.

Persistence: Petals persist, fading with age to shaded from 53C to 53D (R).

Lasting quality: 6 to 8 days when kept at living room temperatures.

*Reproductive organs*

Stamens: Few to many in number, arranged regularly about pistils.

*Anthers.*—Medium, all open at various times. Color—shaded from Yellow-Orange 18A to 18B (R).

*Filaments.*—Medium length, most with anthers. Color—Red Group 50A (R).

*Pollen.*—Abundant. Color—shaded from Yellow-Orange 22C to 22D (R).

Pistils: Medium number.

*Styles.*—Uneven, of medium length, thin to moderately thin and bunched. Color—Shaded from translucent to lighter than Red Group 45D (R).

*Stigmas.*—Color—from Yellow-Orange 22C to 22D (R).

Hips: Long to medium length, globular with conspicuous neck, pear shaped and smooth.

*Walls:* Thick and fleshy. Color—from Tangerine-Orange 9/1 to 9 (N).

Seeds: Many, of medium size.

This new variety of rose plant is an improvement over its unnamed and unpatented seed parent, 15–61R, in its more vigorous growth habit and its production of blooms having improved color and vastly superior flower form. The new variety is also an improvement over its pollen parent "Forever Yours," Plant Patent No. 2,443, in that the cut flower opening stage develops more slowly with a brighter red color and its winter performance shows a marked reduction of blind shoots.

The new plant is a vigorous growing red rose that opens from a dark red bud into a beautiful and brilliant red flower having a rich velvet sheen to its petals. It is a high quality greenhouse rose that performs very well under the low light intensities of winter in the United States latitudes.

I claim:

1. The new and distinct variety of rose plant substantially as herein shown and described, characterized by the range of brilliant red coloring showing in the petalage of its flowers, the relatively slow development of its opening stage, its superior flower form, and its improved performance under the low light intensities of winter months.

No references cited.

ROBERT E. BAGWILL, Primary Examiner